United States Patent [19]

Nair

[11] Patent Number: 5,478,736
[45] Date of Patent: *Dec. 26, 1995

[54] PROCESS FOR THE ISOLATION AND PURIFICATION OF TAXOL AND TAXANES FROM TAXUS USING METHANOL OR ACETONE

[75] Inventor: Muraleedharan G. Nair, Okemos, Mich.

[73] Assignee: Board of Trustees operating Michigan State University, East Lansing, Mich.

[ * ] Notice: The term of this patent shall not extend beyond the expiration date of Pat. No. 5,779,949.

[21] Appl. No.: 297,005

[22] Filed: Aug. 26, 1994

Related U.S. Application Data

[63] Continuation of Ser. No. 126,648, Sep. 27, 1993, abandoned, which is a continuation-in-part of Ser. No. 986,368, Dec. 7, 1992, Pat. No. 5,279,949.

[51] Int. Cl.$^6$ .................. C12P 17/02; C12N 5/04
[52] U.S. Cl. ............... 435/123; 435/240.4; 435/240.46; 435/240.48; 549/510; 549/511
[58] Field of Search ................ 435/123, 240.4, 435/240.46, 240.48; 549/510, 511

[56] References Cited

U.S. PATENT DOCUMENTS 5,019,504  5/1991  Christen et al. .

FOREIGN PATENT DOCUMENTS 9207842  5/1992  WIPO .

OTHER PUBLICATIONS

Gonzalez et al. (1990) Phytochemistry, 29(1), 321–22.

Pavia et al. Organic Laboratory Techniques, CBS College Publishing 1982, 488–89.

Witherup, S., et al., Journal of Natural Products 53, 1249–1255 (1990).

*Primary Examiner*—Irene Marx
*Attorney, Agent, or Firm*—Ian C. McLeod

[57] ABSTRACT

A process for the separation of taxanes, particularly taxol, cephalomannine, baccatin III and deacetylbaccatin III, from ornamental yew tissue is described. The process involves a specific solvent mixture of water and 50 to 95 percent by volume methanol, ethanol or acetone and treatment of the resulting extract using activated carbon, preferably charcoal. The taxanes are preferably separated from the crude extract by a normal phase chromatographic step which preferably is through vacuum and then medium pressure column chromatographic separation, using inexpensive silica gel as an absorbent. The silica gel is regenerated by heating in a furnace above about 500° C. to remove adsorbed organic materials.

19 Claims, 5 Drawing Sheets

NO TAXOL\TAXANES IN FRACTIONS 1-7; FRACTION 8 CONTAIN NON-CHARACTERIZED TAXANES; FRACTIONS 9-11 CONTAIN PURE TAXOL AND CEPHALAMANNINE, FRACTIONS 12-13 CONTAIN BACCATIN III AND OTHER TAXANES.

PROCESS FOR THE ISOLATION AND PURIFICATION OF TAXOL AND TAXANES FROM TAXUS USING METHANOL OR ACETONE

CROSS-REFERENCE TO RELATED APPLICATION

This application is a continuation of application Ser. No. 08/126,648 filed 09/27/93, now abandoned, which is a continuation-in-part of application Ser. No. 07/986,368, now U.S. Pat. No. 5,279,949.

BACKGROUND OF THE INVENTION (1) Field of the Invention

The present invention relates to a process for the isolation and preferably purification of taxol and other taxanes from Taxus spp plant material by using a particular combination of solvent extraction and preferably normal phase chromatographic purification which produces the taxanes in high yield and purity. The process is particularly characterized in the use of preliminary solvent extraction and purification steps which remove the desired taxanes from the plant material without the lipid and chlorophyll components which interfere with the chromatographic purification.

(2) Description of the Prior Art

The production of taxol from ornamental yew needles, barks and roots at present is not economical due to an extremely high percentage of unwanted impurities carried forward in the extract (40–50% by weight of the dried plant material) during the extraction. This unusually high percentage of impurities in the solvent extract of the needles of ornamental yew makes it very expensive and uneconomical to purify taxol and taxanes from this source in addition to the high cost in drying the needles. Published reports suggest that ornamental yew needles contain about 0,002 to 0.01% of taxol on a dry weight basis (Witherup, S., et al., journal of Natural Products 53, 1249–1255 (1990). Organic solvent extraction of 1 kg of the dried ornamental yew needles will afford about 450–500 g of the extract after removing the solvent (45–50% to the biomass) by the published extraction methods using 95% ethanol in water.

The prior art has described taxol and other taxanes isolated from the bark of Taxus spp. which are useful as chemotherapeutic agents, particularly in the treatment of cancers. Illustrative are U.S. Pat. No. 5,019,504 (1991) to Christen et al and WO 92/07842 (1992) to Rao et al. Christen et al describe a cell culture process using *Taxus brevifolia* for producing the taxanes which are then separated by chromatography, by solvent extraction or adsorption methods. Culturing of plant cells is a difficult method for production of the taxanes for use on a large scale. Rao et al describe a process using reverse phase liquid chromatography. The plant material is extracted with a polar solvent, which is 95% by volume ethanol, for 24 hours at ambient temperatures. The 95% by volume ethanol in this step removes many extraneous lipid components and chlorophyll. A solvent-solvent extraction or partitioning step is then used to remove water soluble materials from the water insoluble taxanes. Various solvents are described for the taxanes (chloroform, benzene, ligroin). The solvent is removed to produce a crude extract. This crude extract is then subjected to the reverse phase chromatography in a solvent mixture to isolate the individual taxanes.

There are multiple problems with the Rao et al process. The most important is that plant lipid components and large quantities of chlorophyll are extracted by 95% by volume ethanol. These lipid and chlorophyll components interfere with the separation in the chromatographic column. Also, the crude product is colored from compounds in the plant material and these color compounds interfere with the chromatographic separation. The plant material is preferably dried to less than 0.5% moisture and ground, which aids in the removal of the taxanes during the initial extraction. Drying the Taxus plant material is an expensive step. The extraction process of Rao produces large quantities of crude extract in which taxol and taxanes are only a minor component. The reverse phase chromatographic separation using the process of Rao et al is such that taxol is not cleanly separated. The mother liquor from the initial separation of the taxol is subjected to additional reverse phase chromatography and recrystallization to separate more taxol. The more polar solvent fractions contain 10-deacetylbaccatin III which can be crystallized to remove this compound and then resubjected to standard chromatography. Multiple reverse phrase liquid chromatographic steps may be necessary in the process of Rao et al.

In another disclosed method (FIG. 2) ligroin is used to remove lipid components. Aqueous methanol removes the crude taxane mixture which is then extracted with less polar solvents to separate taxol and related compounds from 10 deactylbaccatin III. The taxanes can be isolated and recrystallized using the reverse phase chromatography. An aqueous methanol extract is partitioned between water and benzene and then extracted with chloroform and the solvents are removed. Methanol or acetonitrile and water is used in reverse phase liquid chromatography to separate the taxanes.

The procedures are set forth in FIGS. 1 to 3 of this reference. None of the procedures provide a clean separation of each of the components in a single pass through a column without a solvent-solvent extraction. Large amounts of various solvents are necessary.

Reverse phase chromatographic separation of impure taxanes from plant materials is very expensive because of the cost of the column materials. Generally reverse phase separation can be used on the bark of Pacific Yew because of the relatively low concentration of pigments, lipids and waxes and high concentration of taxol; however, the yew needles contain lesser amounts of taxol and significant amounts of impurities and thus reverse phase chromatography for separation of taxol from the bulk of the yew materials other than Pacific Yew bark is not practical. There is an urgent need for lower cost production of taxol.

Reverse phase separation is economical only where relatively small numbers of compounds in a mixture are to be separated. A preferred material is silica particles coated with octadecyl silane which is expensive. These particles are used in a column usually at high pressures of between about 50 and 6000 psi and usually with a mixture of acetonitrile and water. In reverse phase chromatography the most polar compounds pass through the column the fastest in contrast to normal phase chromatography.

In normal phase chromatography very inexpensive silica gel is used which is about 100 times or more less expensive than the ordinary reverse phase particles. In normal phase, the silica gel contains silylhydroxide groups (—SiOH) which bind with polar groups of the solute. Thus the more polar compounds move more slowly along the column than less polar compounds. It would be highly desirable to be able to use normal phase chromatography for the separation of taxol and related compounds which are semi-polar; however, to date such columns have not been used because of the large number of polar impurities in the yew plant material, particularly in ornamental yew.

The problem is to simplify the procedures used to produce taxol and other taxane derivatives and reduce the cost using simplified extraction and chromatographic techniques.

OBJECTS

It is therefore an object of the present invention to provide a process for the isolation and separation of taxol and other taxanes from plant materials, preferably fresh material from ornamental yew, in high yield. In particular it is an object of the present invention to provide a process which significantly reduces the cost of production of the taxane derivatives by eliminating the costly drying step, and by reducing the number of steps and the reagents used. These and other objects will become increasingly apparent by reference to the following description and the drawings.

DESCRIPTION OF PREFERRED EMBODIMENTS

The present invention relates to a method for extracting and separating taxanes from plant material of the genus Taxus which comprises: mixing the plant material with an extracting solvent mixture consisting essentially of between about 50% and 95% of a solvent for the taxanes in water by volume so as to extract crude taxane mixture into the extracting solvent mixture; treating the crude taxane mixture in the solvent mixture with activated carbon; removing at least the solvent from the solvent mixture containing the crude taxane mixture; and separating the taxanes from the water and any remaining solvent.

The present invention particularly relates to a method for extracting and separating taxanes from plant material of the genus Taxus which comprises: mixing the plant material with an extracting solvent mixture consisting essentially of between about 50% and 99% of a solvent for the taxanes in water by volume so as to extract crude taxane mixture into the extracting solvent mixture; treating the crude taxane mixture in the solvent mixture with activated carbon; removing at least the solvent from the solvent mixture containing the crude taxane mixture; extracting the crude taxane mixture in a normal phase chromatographic solvent mixture with ethyl acetate; chromatographically separating the taxanes in the chromatographic solvent mixture on a normal phase chromatographic column containing silica gel as an absorbent from the crude taxane at a pressure between about 1 to 15 mm of Hg; separating the taxanes from the chromatographic solvent mixture.

Preferably the plant material is from the needles of an ornamental yew. The plant materials are T. hicksii, T. densiformis, T. gem, T. wardii, T. cuspidata, T. capitata, T. brownii, T. dark green spreader, T. fairview, T. baccata. The plant material is ground in the extracting solvent mixture.

It is particularly preferred to use fresh rather than dried plant material in order to reduce the cost of extraction. The phrase "dried material" means that the plant material is freeze dried, oven dried or air dried, for instance to remove water down to less than about 0.5% by weight. The dried material can be used; however, this significantly increases the cost and over time there is a degradation of the taxanes because of the drying step.

It is preferred that the solvent mixture in step (a) be 70% by volume ethanol in water, particularly with the fresh plant material. Between about 50 to 99 percent can be used providing the amount of activated carbon is increased to remove the chlorophyll, waxes and lipids. Preferably the amount is between 30% to 80% by volume. Less than 50% by volume solvent in water results in poor extraction of the taxanes. Other solvents besides ethanol are methanol or acetone in water in the same manner as ethanol.

Plant extracts normally contain alkanes (waxes) in addition to lipids and chlorophyll. Fresh plant material extracted with organic solvents such as alcohol or acetone contain very high percentages of chlorophyll, lipids and some waxes. However, heat-drying process decompose some of the chlorophyll and extraction of such tissues afford smaller levels of chlorophyll. If the plant tissue is dried by low-temperature lyophilization (freeze-drying) the chlorophyll content will be nearly the same as in the fresh tissue extract.

Activated carbon (charcoal) is used to remove chlorophyll and waxes from plant tissue extracts prior to the separation of the taxanes. Use of the activated carbon (charcoal) is very critical to facilitate the chromatographic separation of the desired active natural product.

The treatment of the extract with activated carbon (charcoal) is an important step to avoid problems in the chromatographic separation. Preferably the carbon has been reactivated by heating in a flame.

In fresh Taxus tissue extraction, charcoal very efficiently removed chlorophyll, the major unwanted material. In dry Taxus tissue extraction, charcoal removed the decomposed chlorophyll as well as the waxes. It is important to use charcoal in both dry and fresh tissue extraction and is the most important step in the method. After extraction of fresh Taxus clippings with 95% by volume ethanol, 4.49 g of chlorophyll and other unwanted materials were removed by charcoaling (about 15% charcoal to the weight of plant tissue) from about 0.5 Kg of tissues. Thus, 8.98 g of contaminants per kg of plant material were removed by the charcoal. If the solvent system is 70% alcohol, the percentage of carbon used was about 5% of the weight of the plant tissue, since much less unwanted materials are extracted. Preferably for fresh plant materials, 5 to 15% by weight of the charcoal based upon the weight of the plant material is used, where the 5% is for 70% solvent and 15% is for 90% solvent. For dried plant materials 20 to 40% by weight based upon the weight of the plant material is used, where 20% is for 70% solvent and 40% is for 95% solvent. Therefore, it is preferred to use the lower percentage of solvent to reduce the amount of activated charcoal which is used.

Similarly, use of ethyl acetate solvent for taxane extraction from the aqueous solution after treatment with charcoal was more effective than using chloroform. Ethyl acetate was found to extract less lipids and non-taxane lipophilic material. EtOAc has a better ability to solvate many polar compounds than chloroform. Since lipophilic material is interfering the purification of taxanes the use of ethyl acetate is important to achieve an efficient and economical isolation and purification of taxanes.

The normal phase chromatographic solvent mixture is preferably ethyl acetate and hexane in an amount between 10 and 90 percent by volume using gradient separation by increasing the amount of ethyl acetate relative to hexane. Other polar and non-polar solvent mixtures can be used as is well known to those skilled in the art. With these solvents low cost vacuum liquid chromatography on silica gel can be used for the separation. Silica is recycled over and over after activating in a furnace at greater than 500° C. to 600° C. which burns off the adsorbed organic materials. A vacuum is used between about 1 and 15 mm of mercury. The final purification to obtain absolutely pure taxol and taxanes can also be achieved by using low to medium pressure (50–100 psi) normal phase chromatography using tandem columns (columns in series). The solvent in this case is a hexane-ethyl acetate gradient system comprising 100% hexane to 50/50 hexane ethyl acetate to 100% ethyl acetate.

A final separation after normal phase chromatography can also be achieved using reverse phase chromatography. The solvent for reverse phase HPLC separation is usually acetonitrile and water. The acetonitrile is preferably between about 50 and 50 percent by volume of the mixture. The column is operated at 500 to 4000 psi.

Figure 1:
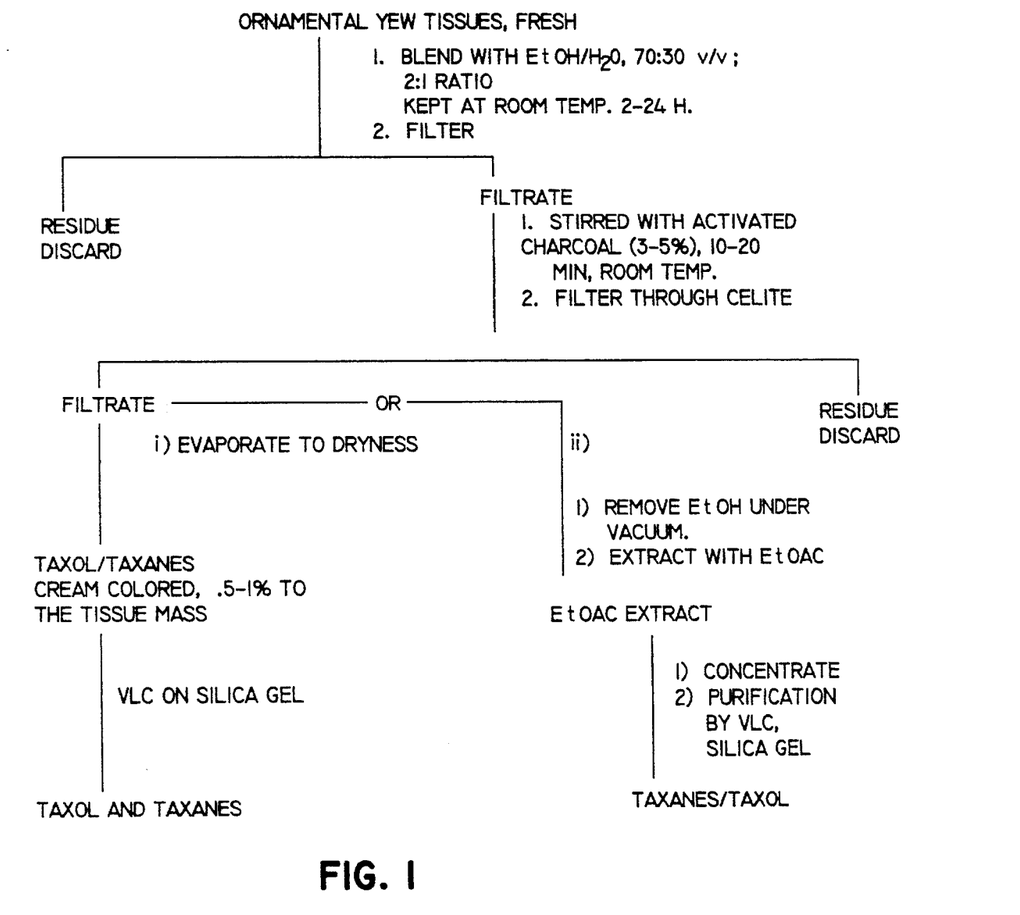
FIG. 1 is a flow chart showing a preferred process of the present invention using activated carbon decolorization and vacuum normal phase liquid chromatography over silica gel.
Figure 2:
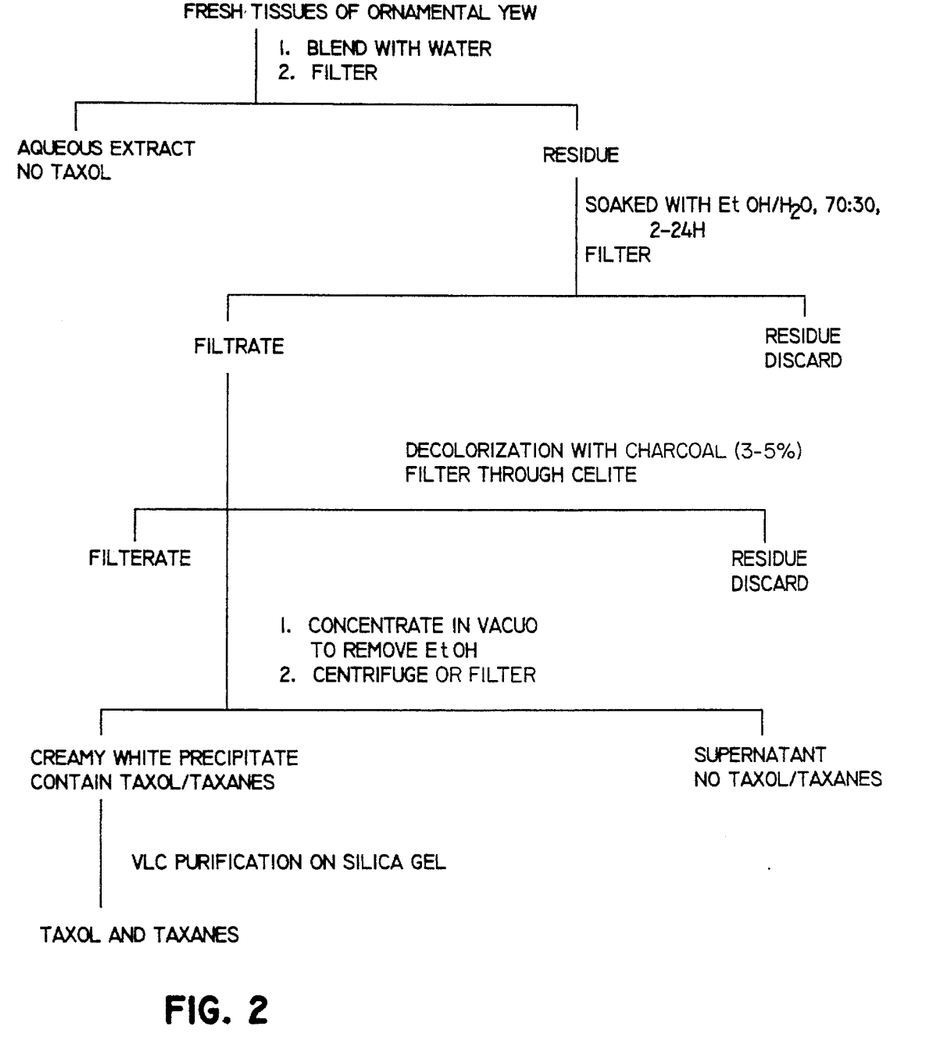
FIG. 2 is a flow chart showing another preferred process of the present invention using activated carbon decolorization and vacuum normal phase liquid chromatography over silica gel.
Figure 3:
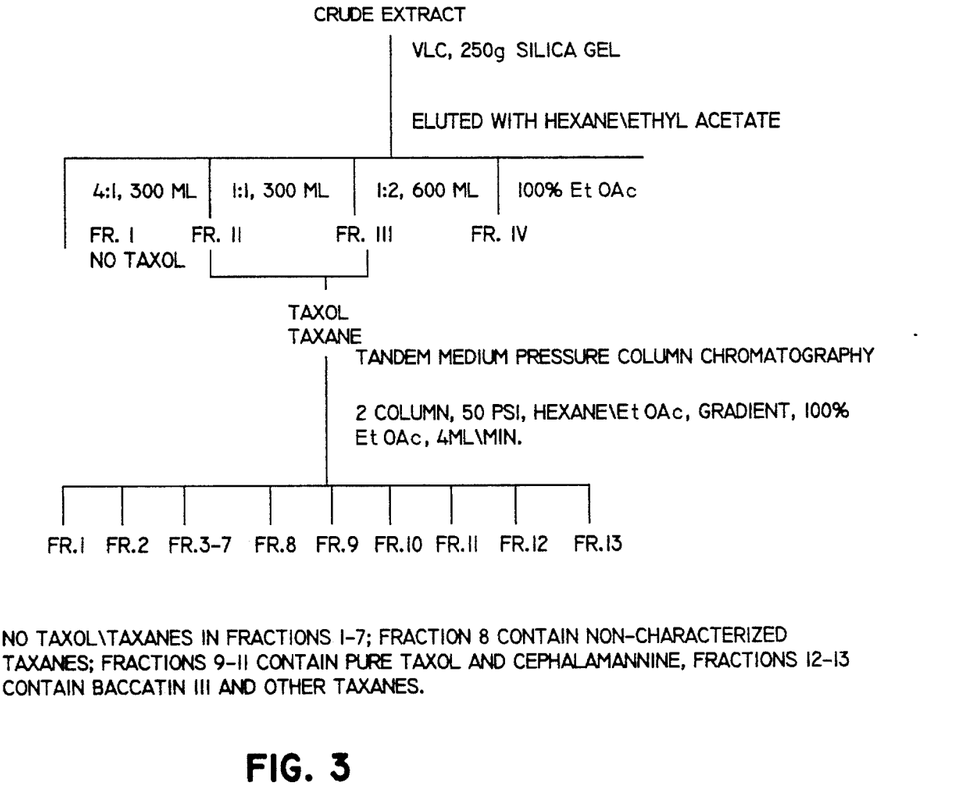
FIG. 3 shows the result of the use of normal phase medium pressure chromatography for separating the products produced by the method of FIG. 1.
Figure 4:
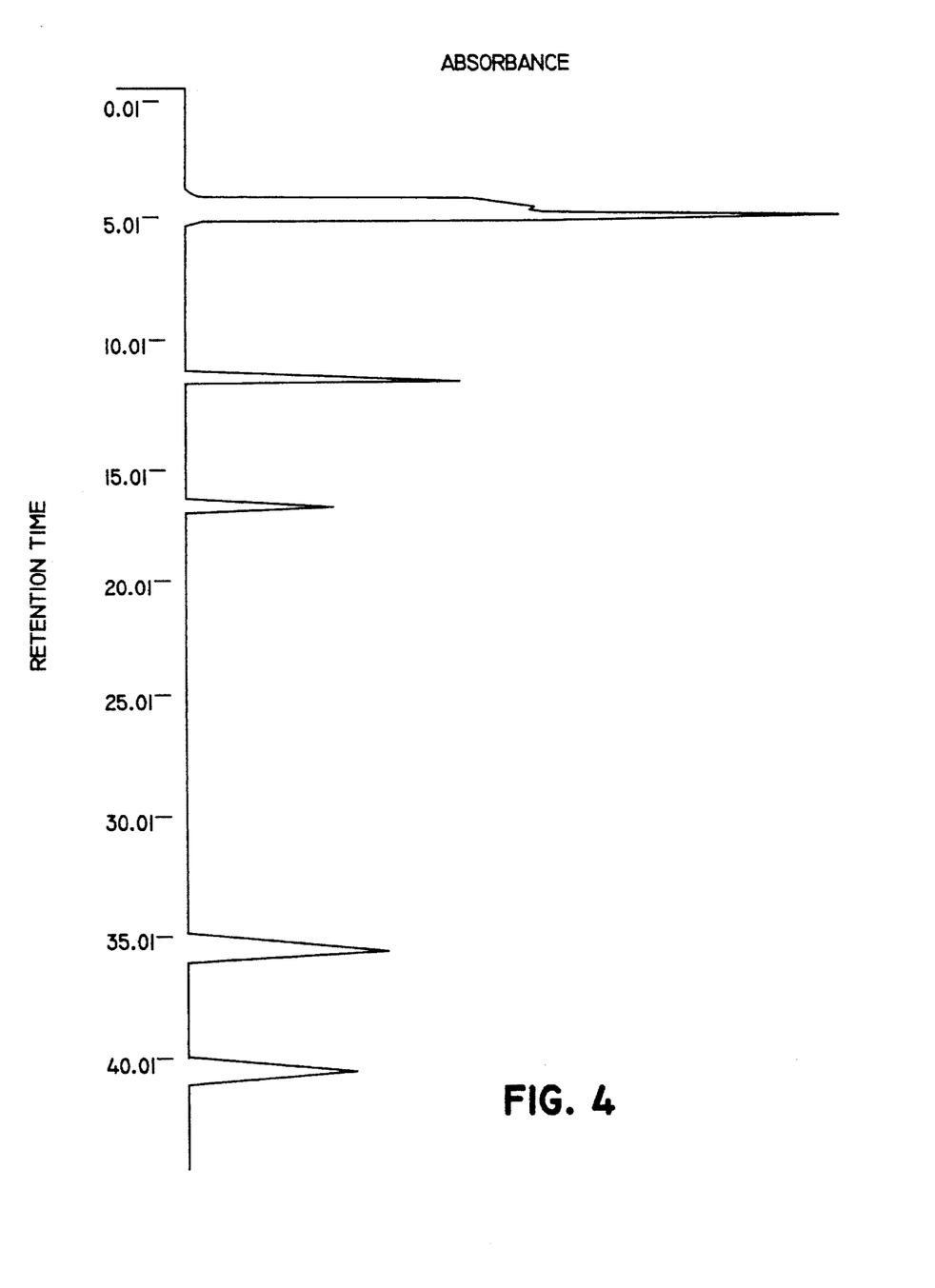
FIG. 4 is a chart showing absorbance versus relative time for reverse phase chromatography of the products of the process of FIG. 3 in Fractions 9 to 11 produced using tandem medium pressure silica column chromatography. The last two fractions are cephalomannine (retention time about 35) and then taxol (retention time about 40).
Figure 5:
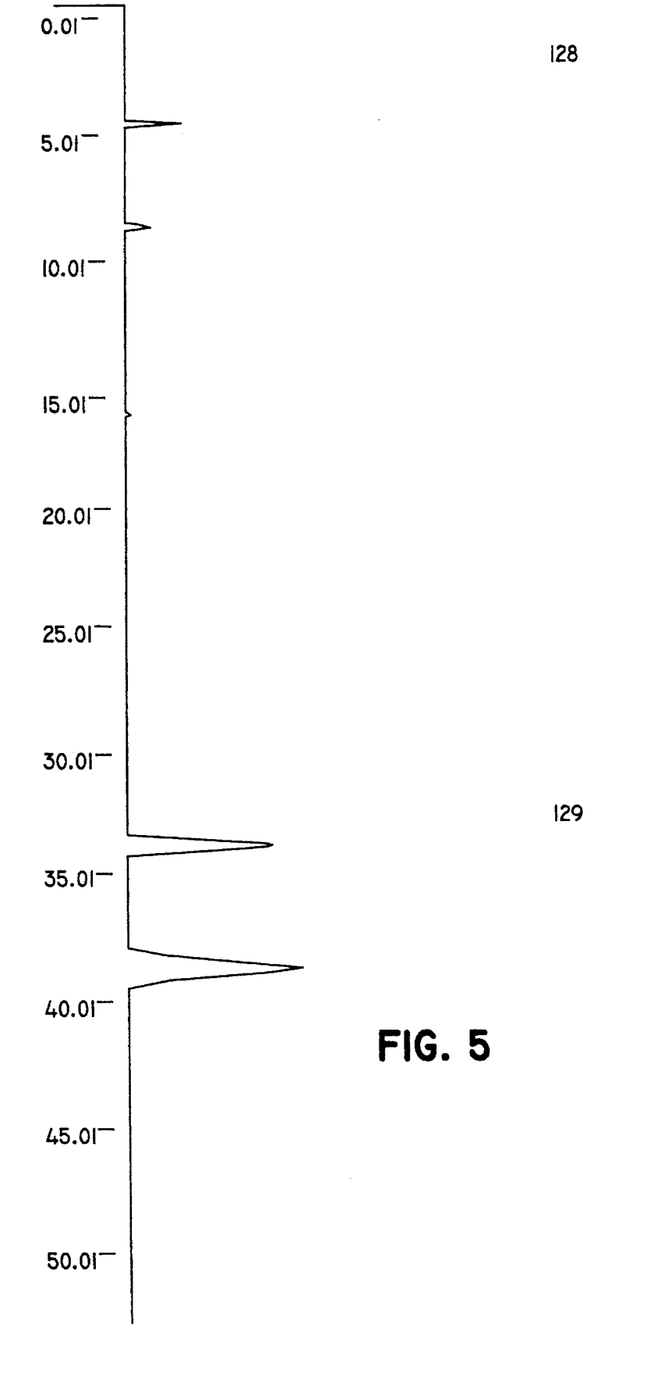
FIG. 5 shows the peaks for cephalomannine (retention time about 35) and for taxol (retention time about 40) for fraction 10 of FIG. 3 showing that the material is taxol and the cephalomannine are produced.

FIGS. 1, 2 and 3 show the extraction step of the present invention which produces 0.5–1% extract of the biomass. FIGS. 4 and 5 show the chromatographic separation achieved by the processes of FIGS. 1, 2 and 3.

The extraction process of the present invention can use 50 to 95% by volume ethanol in water. The higher amounts above 80% of the extraction solvent are preferably used with the dried materials since the dried tissue is solvated poorly by higher concentrations water. However, more charcoal is needed where high amounts of solvent are used.

Yew tissues can be needles, stem, bark, whole plant or roots separately or as a mixture. The tissues can be fresh or dried. Use of fresh material eliminates the high cost involved in drying process prior to the extraction of the taxanes. The reported preferred prior art procedure involves the use of dried material since lipophilic solvents are used for the extraction.

Pressing or grinding the fresh tissue with water and removal of the aqueous extract itself is a preferred purification step prior to the extraction since water removes proteins, sugars, and organic and inorganic salts present in the yew tissues. The taxanes are insoluble in water.

In the preferred process, the taxanes are soluble in 50–99% ethanol, acetone or methanol in water as the extraction solvent, and hence the tissues are ground or mixed with the solvent. The preferred higher percentage of water (20 to 50%) used in the extraction (compared to the 5% reported by Rao et al) retains the waxes, much of the chlorophyll and lipophilic compounds in the tissue and are not carried into the extract. Usually the plant tissue is soaked for 2 to 24 hours.

The extract solution is preferably evaporated to remove the extraction solvent and to precipitate the taxanes which are insoluble in water and then the precipitate is filtered from the solution. The aqueous portion containing the taxane/taxol precipitate can be centrifuged to collect the precipitate of the taxanes. This step also removes all the water soluble impurities carried forward during the extraction with aqueous extraction solvent. Alternatively, the water can be removed along with the ethanol, although this is not preferred.

The initial separation of taxol and other taxanes is achieved on ordinary inexpensive column silica gel, which is regenerated, rather than the expensive reversed phase absorbents which cannot be regenerated. Final purification of taxol from the cephalomannine and taxol mixture to obtain 100% purity can be achieved by recrystallization or by purification by medium normal tandem column chromatography using ethyl acetate hexane in a gradient medium pressure silica column. Reverse phase chromatography using a pressure between about 50 and 4000 psi and the "CAPCELL" C-18 particles (Shiseido Co., Ltd., Tokyo, Japan) can also be used for the final separation as shown in FIGS. 4 and 5, although this is expensive. One method uses a 10×250 mm column and a 50–50 mixture by volume of acetonitrile and water at a flow rate of 1.5 ml per minute. The column is operated at 1360 psi. The system uses 0.1 AUFS (absorbance units full scale) at a lambda of 210 mm. In FIG. 4 the first peak is solvent, the second peak is 10 deacetylbaccatin III, the third peak is baccatin III, the fourth peak is cephalomannine and the fifth peak is taxol. FIG. 5 shows only cephalomannine and taxol from fraction 10 in FIG. 3.

The following are Examples of the method of the present invention.

EXAMPLE 1

As shown in FIG. 1, fresh clippings of Taxus hicksii (1.5 Kg) was blended with ethanol (EtOH) (70%, 3L) in a commercial Waring blender (Thomas Scientific, Swedesboro, N.J.) for 3 minutes. The mixture was kept at room temperature for two (2) hours. It was filtered through cheesecloth and the filtrate was centrifuged (10 minutes, 4° C., 10,000 g) and the supernatant was decanted. The green colored supernatant was mixed with activated carbon (charcoal; 100 g) and stirred at room temperature for 20 minutes. The solution was filtered through celite (diatomaceous earth) in a sintered glass filter. The resulting near colorless solution was evaporated under reduced pressure to remove the ethanol and the aqueous portion was extracted with ethyl acetate (EtOAc) (2×200 ml). The EtOAc was then removed to leave a solid. As shown in FIG. 3, the cream colored solid (3 g) was dissolved in EtOAc (50 ml) and fractionated by silica gel vacuum liquid chromatography (300 g column silica gel) using a hexane EtOAc gradient system ending in 100% EtOAc. The fractions were: I (600 ml, hexane 100%), II (400 ml, 4:1 hexane-EtOAc), III (600 ml, 1:1 hexane EtOAc) and IV (600 ml, EtOAc 100%). Taxol and taxanes were in fraction III by HPLC analysis. Fraction III was further purified by tandem silica gel column medium pressure (30–45 psi) chromatography using a hexane-EtOAc gradient system to obtain pure taxol and taxanes. The fractions from the medium pressure column chromatography were: I (50 ml, 1:1 hexane-EtOAc), II–VII (25 ml each, 100% EtOAc), VIII–XIII (10 ml each, 100% EtOAc), XIV–XV (25 ml each, 100% EtOAc). Fractions I–VII did not contain taxol/taxanes by HPLC analyses. Fractions VIII–X gave white powders upon removal of the solvent and contained pure cephalomannine, taxol and some uncharacterized taxanes. Fractions XI–XIII contained baccatin-III and deacetylbaccatin-III. The individual fractions were separated by HPLC.

EXAMPLE 2

FIG. 2 shows an alternate process wherein the taxols are removed from the water by centrifugation after the EtOH is removed. The taxanes including taxol precipitate since they are insoluble in water. The process is otherwise identical to Example 1.

EXAMPLE 3

Fresh Roots of ornamental yew, *T. hicksii*: The roots from *T. hicksii* were washed with water immediately after they were dug to remove the soil. The washed fresh roots (100g) were blended in an Industrial Waring blender with 70:30 v/v ethanol-water, by volume, (400 ml, 2 min). The mixture was kept for 2 hours at room temperature and filtered and then the residue was washed with another 100 ml 70/30 ethanol-water mixture. The combined filtrate was decolorized with activated charcoal (10 g) and filtered through celite. The filtrate was evaporated to remove ethanol and the aqueous portion was extracted with ethyl acetate (50 ml ×3). The combined ethyl acetate fractions were dried in vacuo and afforded 0,802 g of dried extract containing taxol and taxanes.

EXAMPLE 4

Dried Roots of *T. hicksii*: The roots of Example 3 were dried in an oven at 45° C. for two (2) days and milled. Twenty-five grams (25 g) of this powder was processed by stirring with 100 ml of 70/30 ethanol-water, by volume, for 45 min and then filtered. The residue was extracted with the same solvent mixture for two more times and the combined extract was centrifuged for 10 min at 4° C. at 10,000 rpm. The supernatant was processed as in Example 3. The weight of extract was 0.857 g.

EXAMPLE 5

Fresh bark from *T. hicksii*: Twenty-five (25 g) of tissue was blended with 130 ml of 70/30 ethanol-water, by volume, treated with 2.5 g charcoal, and then extracted with 10 ml ×3 ethyl acetate as in Example 3. The dried extract weight was 0.135 g.

EXAMPLE 6

Dried Bark from *T. hicksii*: The dried bark was processed as in Example 4. The weight of crude extract was 1,096 g.

EXAMPLE 7

Dried *T. hicksii* clippings of *T. hicksii*: The clippings were dried in an oven at 45° C. for two (2) days and milled. Twenty-five (25) g tissue was stirred with 70/30 ethanol-water, by volume, (100 ml) and filtered after 45 minutes. This was repeated two more times and the combined extract was centrifuged (10,000 rpm, 4° C., 10 min) and the supernatant was decanted. The supernatant was decolorized with 2.5 g charcoal and processed as in Example 3. The weight of extract was 0,903 g.

COMPARATIVE EXAMPLE 8

Rao's process with fresh roots: One hundred grams (100 g) of fresh roots were blended with 95/5 v/v ethanol-water, by volume, mixture (400 ml), kept at room temperature for 2 hours, filtered and washed the residue with another 100 ml of the solvent mixture. The combined extract was evaporated to remove ethanol and the residue was extracted with trichloromethane. However, there was an inseparable emulsion. Saturated sodium chloride solution (150 ml) was used to separate the trichloromethane layer (150 ml) from the emulsion (@ 2 h), although this was not disclosed by Rao. The organic layer was removed and dried in vacuo to afford 1.12 g of dried extract.

COMPARATIVE EXAMPLE 9

Dried Roots of *T. hicksii*: Twenty-five grams (25 g) of dried roots were extracted with 95/5 ethanol-water, by volume, mixture and processed as in Example 8. The weight of the extract was 0,305 g.

COMPARATIVE EXAMPLE 10

Fresh bark from *T. hicksii*: Twenty-five grams (25 g) of tissue was extracted with 130 ml of 95/5 ethanol-water and the aqueous portion was extracted with 30 ml chloroform as in Example 8. The crude residue was 0,158 g.

COMPARATIVE EXAMPLE 11

Dried bark from *T. hicksii*: Dried bark was processed as in Example 8. The weight of crude extract was 0.532 g.

COMPARATIVE EXAMPLE 12

Dried clippings from *T. hicksii*: Twenty-five grams (25 g) of tissue was extracted 3 times with 95/5 ethanol-water, by volume, mixture and centrifuged. The supernatant was evaporated and the aqueous residue was extracted with chloroform as in Example 8. An inseparable emulsion was obtained. Addition of saturated sodium chloride brine separated the organic layer. The weight of extract was 0,995 g.

Comparative Examples 8 to 12 produced product which was heavily contaminated with non-taxane materials, particularly lipids and waxes, because of the use of trichloromethane for the extraction. These extracts were unsuitable for direct chromatographic purification. By contrast, the products of Examples 1 to 7 were well suited to direct chromatographic separation by the method of the present invention.

All of the extractions of Examples 1 to 7 were also carried out in methanol/water and acetone/water mixtures and the results were similar to ethanol-water mixture. Therefore, these solvents-water mixtures can be substituted for ethanol-water mixtures.

For dried bark, root and clippings the preferred ratio of the extraction solvent was 95/5 solvent-water by volume. The resulting extract was then treated with activated charcoal and preferably concentrated in vacuo to remove ethanol and extracted three times with ethyl acetate. The combined ethyl acetate extracts was evaporated to dryness to afford highly pure fraction containing all the taxanes of interest. The taxanes can also be removed by centrifugation or filtration from the aqueous solution remaining after removal of the solvent.

EXAMPLE 13

Needles, stems and clippings of *Taxus x media* "Hicksii" were stored up to 21 days at 4 and 25°, respectively, to determine the effect of storage conditions on taxol and cephalomannine. The taxanes were then separated by the process of the present invention. Taxol levels were significantly higher in plant material stored at 4° when compared to levels at harvest and materials stored at 25°. Taxol content, when compared to the tissues at harvest, was appreciably higher in tissues stored at both 4 and 25° over 7 days while cephalomannine showed a decline during storage at 25°. However, cephalomannine content was higher in clippings during the first week of storage at 4°. Also, an overall declining trend was observed for taxol and cephalomannine in all tissues after 7 days of storage irrespective of the storage temperature. These results indicated that a delay in processing fresh plant biomass by storing them at 4° for 7 days from harvest to extraction should enhance taxol and cephalomannine yields. Based upon this experimental data, it was determined that a preferred time of storage was 7 to 10 days and a preferred temperature range was 0° to 10° C. to increase the taxol content of the plant tissue prior to treatment by the method of the present invention.

It is intended that the foregoing description be only illustrative of the present invention and that the present invention be limited only by the hereinafter appended claims.

I claim:

1. A method for extracting and separating taxanes including taxol from plant material of the genus Taxus which comprises:
   (a) mixing fresh clippings of the plant material with an extracting solvent mixture consisting essentially of between about 50% and 80% of an organic solvent selected from the group consisting of acetone and methanol in water mixture by volume so as to extract a crude taxane mixture in the extracting solvent mixture;
   (b) decolorizing the crude taxane mixture in the solvent mixture with charcoal;
   (c) removing at least the acetone or methanol from the solvent mixture containing the crude taxane mixture;
   (d) extracting the crude taxane mixture in a normal phase chromatographic solvent containing ethyl acetate;
   (e) chromatographically separating the taxanes in the chromatographic solvent mixture on a normal phase chromatographic column containing silica gel as an absorbent for the crude taxane at a pressure which provides the separation between about 1 mm of mercury and 100 psi;
   (f) separating the taxanes from the chromatographic solvent mixture.

2. The method of claim 1 wherein the solvent in step (a) is 70% by volume acetone or methanol in water.

3. The method of claim 1 wherein the fresh clippings are from an ornamental yew.

4. The method of claim 3 wherein the ornamental yew is selected from the group consisting of *T. hicksii, T. densiformis, T. gem, T. wardii, T. cuspidata, T. capitata, T. brownii, T. dark green spreader, T. fairview.*

5. The method of claim 1 wherein in step (e) an additional column is operated at a pressure between about 50 to 100 psi after the separation at 1 to 15 mm Hg.

6. The method of claim 1 wherein the solvent in step (a) is 70% by volume acetone or methanol in water and the column is operated under a vacuum.

7. The method of claim 1 wherein the taxanes in step (f) are selected from the group consisting of taxol cephalomannine, baccatin-III and 10-deacetylbaccatin III.

8. The method of claim 1 wherein after step (f) the taxanes are separated from each other by a high pressure reverse phase chromatography column of octadecylsilane coated on teflon silica and wherein the solvent mixture is a mixture of acetonitrile and water.

9. The method of claim 8 wherein the chromatographic solvent mixture is about 50% by volume acetonitrile.

10. The method of claim 8 wherein the pressure in the reverse phase chromatography column is between about 50 and 4000 psi.

11. The method of claim 1 wherein the crude extract from step (c) is further extracted with ethylacetate and then the ethylacetate is partially removed prior to step (d) and wherein in step (d) the solvent is the ethylacetate and hexane.

12. The method of claim 1 wherein in step (e) multiple columns containing normal phase silica absorbent are used in series after the separation at 1 to 15 mm Hg.

13. The method of claim 1 wherein the fresh clippings are ground with water and then the water is removed from the fresh clippings prior to mixing the solvent mixture with the fresh clippings in step (a), 14. The method of claim 1 wherein the fresh clippings are soaked in the solvent in step (a) for 2 to 24 hours at ambient temperatures before step (b).

15. The method of claim 1 wherein in step (c) the crude taxane mixture precipitates in the water remaining after the removal of the acetone or methanol and wherein the crude taxanes are separated from the water.

16. The method of claim 1 wherein in step (c) the water and the acetone or methanol are removed from the crude taxane mixture.

17. The method of claim 1 wherein the fresh clippings are ground in the solvent mixture in step (a).

18. The method of claim 1 wherein the organic solvent is acetone.

19. The method of claim 1 wherein the organic solvent is methanol.

* * * * *